United States Patent [19]

Engler et al.

[11] 4,362,662
[45] Dec. 7, 1982

[54] HETEROFULVALENE GEMINAL DITHIOLATE COMPOUNDS AND THEIR SELENIUM AND TELLURIUM ANALOGS AND A METHOD OF FABRICATING THE SAME

[75] Inventors: Edward M. Engler, Wappingers Falls; Vishnubhai V. Patel, Yorktown Heights, both of N.Y.; Robert R. Schumaker, San Jose, Calif.

[73] Assignee: International Business Machines Corporation, Armonk, N.Y.

[21] Appl. No.: 293,565

[22] Filed: Aug. 17, 1981

Related U.S. Application Data

[62] Division of Ser. No. 38,050, May 10, 1979, Pat. No. 4,312,991.

[51] Int. Cl.$^3$ .......................................... C07D 421/04
[52] U.S. Cl. ................................................. 260/239 R
[58] Field of Search ..................................... 260/239 R

[56] References Cited

FOREIGN PATENT DOCUMENTS 2739584  6/1978  Fed. Rep. of Germany ........ 549/39

*Primary Examiner*—Robert Gerstl
*Attorney, Agent, or Firm*—Joseph G. Walsh

[57] ABSTRACT

The invention is directed to novel heterofulvalene geminal dithiolate compounds and their selenium and tellurium analogs having the general formula

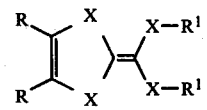

wherein X is selected from S, Se and Te. R is selected from hydrogen, alkyl, aryl, or together form a ring of carbon atoms, cyano and dithiocarbonate groups and $R^1$ is selected from alkali, alkaline earth and transition metals, alkyl, aryl, cyclic and heterocyclic groups.

A novel method for preparing these compounds is also provided.

1 Claim, No Drawings

HETEROFULVALENE GEMINAL DITHIOLATE COMPOUNDS AND THEIR SELENIUM AND TELLURIUM ANALOGS AND A METHOD OF FABRICATING THE SAME

This is a division of application Ser. No. 038,050 filed May 10, 1979, now U.S. Pat. No. 4,312,991.

BACKGROUND OF THE INVENTION

1. Field of the Invention

The present invention is directed to novel heterofulvalene geminal dithiolate compounds and their selenium and tellurium analogs derivatives thereof. These compounds are key synthetic intermediates for the preparation of tetrathiafulvalene derivatives and tetraselenafulvalene derivatives which are useful in optical printing of conducting patterns, in electrochromic displays and in high resolution lithography.

2. Prior Art

It is well known that charge transfer salts containing the organic donors tetrathiafulvalene or selenium analogs tetraselenafulvalenes are the most electrically conducting organic solids (see Coleman et al Solid State Commun. 12, 1125 (1973) and U.S. Pat. No. 4,028,346 to Engler et al). U.S. Pat. No. 4,089,857 to Engler et al discloses the synthesis of tetrathiapentalene and tetraselenapentalene compounds which are used as intermediates for the preparation of tetrathiafulvalene and tetraselenafulvalene, respectfully.

As far as we are aware, the heterofulvalene geminal dithiolate compositions of the present invention are novel. Related structures have been described previously. For example, see a review by D. Coucouvanis in Progress in Inorganic Chemistry, Vol. 11, p. 233, 1970 and publications by Jensen and Henriksen, Acta Chem. Scand., 22, 1107 (1968) and 23, 3213, (1970) ibid.

The above cited prior art does not however, disclose the compositions of this invention, their synthesis or their chemical conversion to novel tetraheterofulvalene derivatives.

SUMMARY OF THE INVENTION

The overall synthetic procedure for the preparation of compounds of the present invention is outlined below.

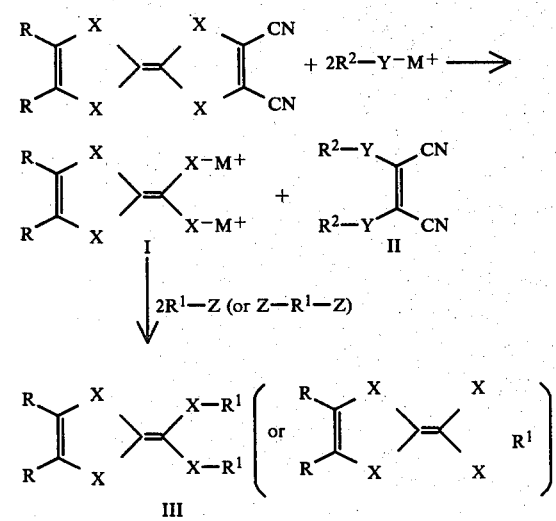

where;
R=H, alkyl, aryl, where R units are connected in a cyclic or heterocyclic structure (e.g. benzo: —CH=CH—CH=CH—, trimethylene: —CH$_2$—CH$_2$—CH$_2$—; dithiocarbonate:

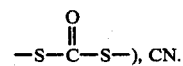

), CN.

X=S, Se.
R$^2$=alkyl, aryl, acyl, or where the two mole equivalents are in the same molecule as in M$^+$−Y-R$^2$-Y$^-$M$^+$ (e.g. salts of orthodithiobenzene or 1,4-butanedithiol, etc.)
Y=S, Se, Te
M=alkali metal (Li$^+$, Na$^+$, K$^+$), quarternary ammonium (e.g. trialkylammonium such as (CH$_3$)$_3$NH$^+$, (CH$_3$CH$_2$)$_3$NH$^+$, etc.)
R$^1$=alkali metal ion (Li$^+$, Na$^+$, K$^+$), alkaline earth metal ion (Mg$^{+2}$, Ca$^{+2}$), transition metal ion (Ni$^{+2}$, Fe$^{+3}$, Pd$^{+2}$, Cu$^{+2}$, etc.), alkyl, also alkyls having unsaturated groups such as propargyl: —CH$_2$—C≡CH, ketones (e.g. cyclopentanone), aryl groups (e.g. phenyl, etc.), and wherein R$^1$ units are connected in a cyclic or heterocyclic structure (e.g. where two mole equivalents of Z are in the same molecule: Z-R$^1$-Z such as in 1,2-dibromoethane, 1,2-dichloroethyl ether, etc.).
Z=Cl, Br or I The first step of the method of preparing the composition of the present invention involves the reaction of a cis-dicyanotetraheterofulvalene derivative with two equivalents of an organic sulfide, selenide or telluride compound which is typically generated by reaction of the corresponding chalocogen alcohol (i.e. R$^2$-YH) with bases (such as trialkylamines, KOH, KH, etc.) or by reaction of the elemental chalcogen with an alkyl metal salt (such as n-butyl lithium) phenyl magnesium bromide, etc. The reaction can be carried out in a variety of solvents including acetonitrile or dimethylformamide. The reaction to give compounds I and II above is complete in a few minutes at room temperature. Sometimes it is necessary to cool the reaction to about 0° C. depending on the nature of R. For example, when R units are connected by a dithiocarbonate

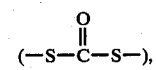

cooling to 0° C. is required. Because geminal dithiolates are easily oxidized, reactions are typically carried out in an inert atmosphere, e.g. under nitrogen or argon. Compounds I and II can be separated at this stage, or kept in situ to be reacted in the second step with R$^1$-Z (or Z-R$^1$-Z) to give compound III above. The second step is also carried out at room temperature, and is usually completed in a couple of minutes. In some cases, depending on the nature of functional groups in R$^1$, subsequent chemical treatment may be more desirable than isolation of compound III. For example, reaction of I with α-haloketones provides alcohol derivatives of compound III which are readily converted to tetrathiafulvalenes on treatment with strong acids (e.g., H$_2$SO$_4$, HClO$_4$, etc.) as shown below:

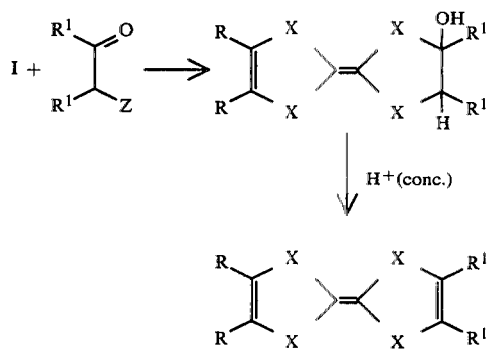

We have found that the reactions leading to compounds I, II and III to be quite general and to proceed in excellent yields, e.g. typical yields=50%-80%, in most cases. Reactions where X and Y are sulfur give the best yields, while when Y is selenium or tellurium lower yields e.g., 30–50% are obtained.

The reaction of tetrathiafulvalenes with $R^2\text{-}Y^-M^+$ to give geminal dithiolate salts and compounds is specific to cis-dicyano substituted tetrathiafulvalenes. For example, other electron withdrawing substituents such as trifluoromethyl ($-CF_3$) or carbomethoxy ($-CO_2CH_3$) in tetraheterofulvalenes do not give geminal dithiolate compound I.

Furthermore, the reaction of cis-dicyanotetrathiafulvalenes with sulfides is very selective and proceeds even in the presence of other base sensitive functional groups. For example, cis-dicyanodithiocarbonatetetrathiafulvalene, (also named: 2,3-dicyano-6,7-(2'-oxo-1'3'-dithioleno)-(4',5'-h)-tetrathiafulvalene, see structure IV) reacts only at the dicyanoethylene end of the molecule and not at the base sensitive dithiocarbonate group to give compound V which is isolated as the methyl derivative by addition of methyl iodide to give, dithiomethyl-(4,5-(2'-oxo-1',3'-dithioleno)-1,3-dithioliden-2-yl) methylene (see structure VI).

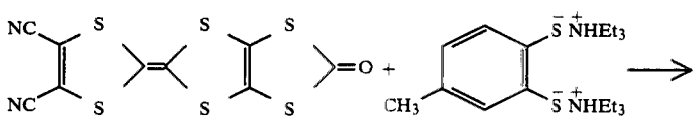

IV

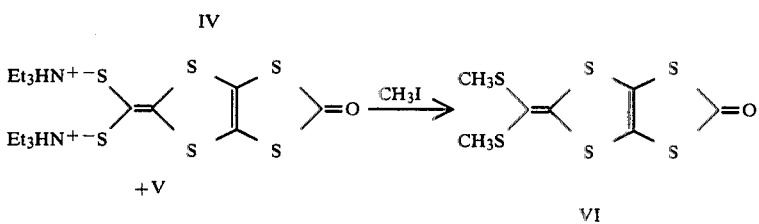

+V              VI

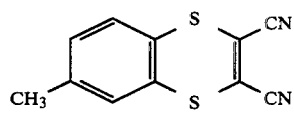

Reaction of V, with sodium methoxide or methyl lithium leads to reaction at the dithiocarbonate group to give a 1,2-dithiolate intermediate which is reacted with transition metal salts such as nickel acetate and then oxygen to give the novel bis-dithiolene VII (shown below) which displays an unusual, low-energy, strong electronic absorption (at $1.4\mu$) and is useful in Q-switch applications for lasers.

VI + 2NaOCH$_3$ ⟶

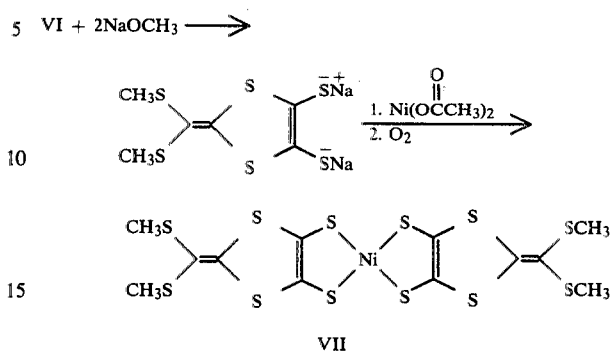

VII

By appropriate choice of $R^1$, compounds I and III can be further reacted to a variety of materials which possess useful and novel electrical and optical properties. For example, treatment of tetracyanotetrathiafulvalene with two mole equivalents of a sulfide, followed by addition of an α-chloroketone and treatment with concentrated acid gives the unsymmetrically substituted tetrathiafulvalene VIII as shown below:

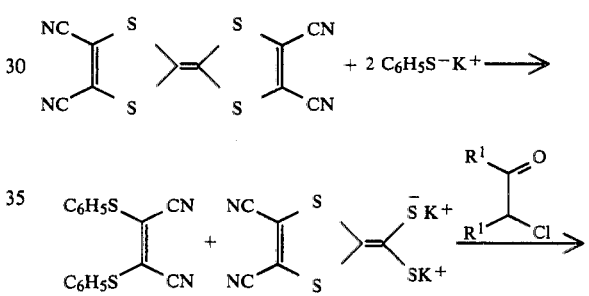

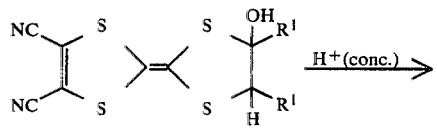

-continued

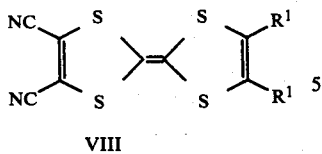

VIII

In another example, reaction of tetracyanotetrathiafulvalene with two mole equivalents of a sulfide, followed by addition of 1,2-dichloroethyl ether gives compound IX which on treatment with acid and heat provides the unsymmetrical dicyanotetrathiafulvalene X as shown below:

-continued

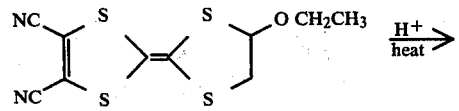

IX

X

Unsymmetrical cis-dicyanotetrathiafulvalenes such as compounds VII and X are of interest since they can be converted to novel phathalocyanine derivatives illustrated below:

R=H, alkyl, phenyl, etc.
M=Ni, Cu, Fe, Pt, etc.

The geminal dithiolate salts described by formula I are air-sensitive and have to be handled under inert atmosphere conditions. They are easily oxidized by oxygen, iodine, peracids, and the like to give coupled products which undergo myraid of complex chemistry. For example:

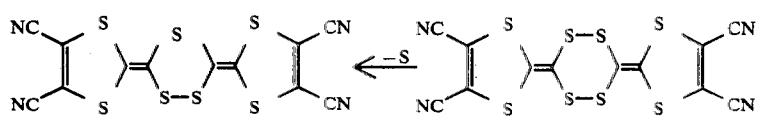

Because of this sensitivity of I to air-oxidation it is generally preferable to immediately react I in situ with further reagents of the type $R^1$-Z (or Z-$R^1$-Z). In this connection, while a variety of $R^1$ groups are successfully reacted to give compounds of the type described by formula III, those which are easily reducible are not appropriate. For example, treatment of geminal dithiolate salt I (X=S, R=CN, M=K) with chloranil does not lead to displacement of the chlorines but to reduction of chloranil to its stable radical anion salt as shown below:

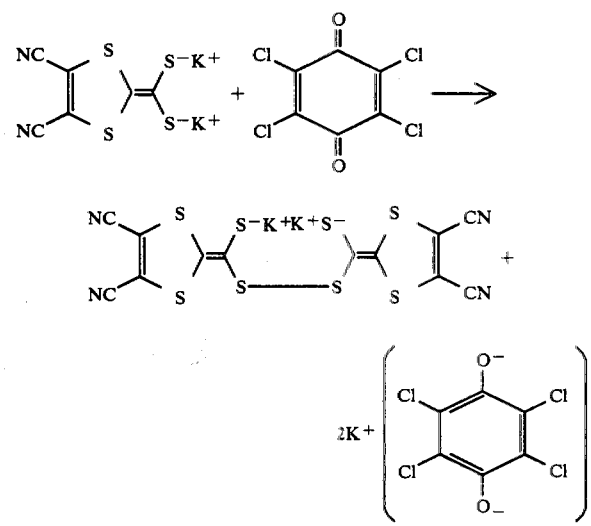

A useful alternative to handling salts of I is to react them with acyl derivatives to give compounds of the general formula XI. These thioesters can be stored and reacted as needed with base to generate the geminal dithiolate salt again, for example, as shown below:

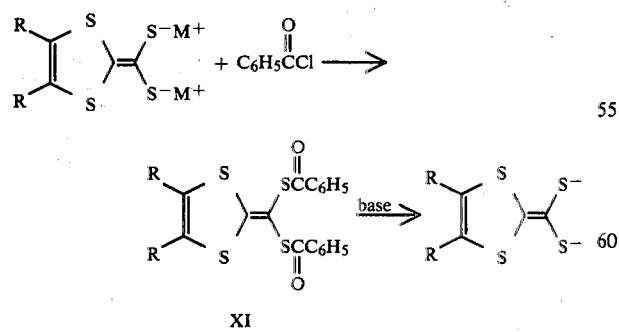

XI

The following examples are given solely for purposes of illustration and are not to be considered limitation on the invention, many variations of which are possible without departing from the spirit or scope thereof.

EXAMPLE 1

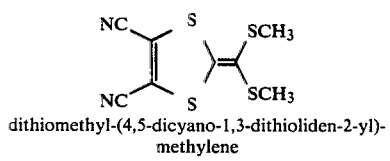

dithiomethyl-(4,5-dicyano-1,3-dithioliden-2-yl)-methylene

To one mole equivalent of tetracyanotetrathiafulvalene, dissolved in nitrogen-purged acetonitrile, is added two mole equivalents of triethylamine and one mole equivalent of o-toluenedithiol under nitrogen with stirring. Excess methyl iodide is added, and the solvent evaporated. The reaction mixture is then chromatographed (silica gel, chloroform-hexane) to give dithiomethyl-(4,5-dicyano-1,3-dithioliden-2-yl)-methylene as a purple-red solid; mp 126° C.; analysis for $C_8H_6N_2S_4$, calcd %C:37.20, %H:2.32, %N:10.85, %S 49.61, found %C:37.21, %H:2.27, %N 10.84, %S 49.57. A by-product from this reaction was also isolated and identified as 2,3-dicyano-5,6-(3'-methylbenzo)-1,4-dithiene: yellow solid; m.p. 180° C.; analysis for $C_{11}H_6N_2S_2$, calcd %C:57.39, %H:2.60, %N:12.17; %S:27.82, found %C:57.29, %H:2.75, %N:11.73, %S:26.63.

EXAMPLE 2

The same reaction conditions as provided in Example 1 are followed, except two mole equivalents of methylthiol are used in place of one mole equivalent of o-toluenedithiol. Work up of the reaction mixture gave dithiomethyl-(4,5-dicyano-1,3-dithioliden-2-yl)-methylene and as the by-product: 1,2-dithiomethyl-1,2-dicyanoethylene.

EXAMPLE 3

The same reaction conditions as provided in Example 1 are followed, except two mole equivalents of phenylthiol are used in place of one mole equivalent of o-toluenedithiol. Work up of the reaction mixture gave dithiomethyl-(4,5-dicyano-1,3-dithiolen-2-yl) methylene and as the by-product 1,2-dithiophenyl-1,2-dicyanoethylene.

EXAMPLE 4

The same reaction conditions as provided in Example 1 are followed, except two mole equivalents of sodium thioacetate

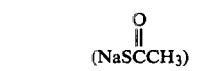

are used in place of triethylamine and o-toluenedithiol. Work-up of the reaction mixture gave dithiomethyl-(4,5-dicyano-1,3-dithioliden-2-yl)-methylene.

EXAMPLE 5

The same reaction conditions as provided in Example 1 are followed, except two mole equivalents of lithium n-butylselenide are used in place of triethylamine and o-toluenedithiol. Work up of the reaction mixture gave dithiomethyl-(4,5-dicyano-1,3-dithiolen-2-yl) methylene.

EXAMPLE 6

The same reaction conditions as provided in Example 1 are followed, except two mole equivalents of lithium n-butyltelluride are used in place of triethylamine and o-toluenedithiol. Work up of the reaction mixture gave dithiomethyl-(4,5-dicyano-1,3-dithioliden-2-yl) methylene.

EXAMPLE 7

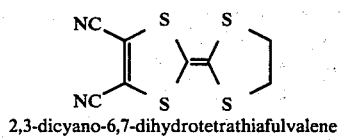

2,3-dicyano-6,7-dihydrotetrathiafulvalene

To one mole equivalent of tetracyanotetrathiafulvalene, dissolved in nitrogen-purged acetonitrile, is added two mole equivalents of potassium thioacetate dissolved in anhydrous methanol. After stirring 10 minutes, a solution of one mole equivalent of 1,2-dibromoethane in acetonitrile is added dropwise. The reaction mixture is then heated to reflux for ½ hour. Evaporation of the solvent gave a dark oil which was dissolved in acetone and chromatographed (silica gel, hexane-benzene) to give 2,3-dicyano-6,7-dihydrotetrathiafulvalene as a purple solid; mp 230°–232° C.; analysis for $C_8H_4N_2S_4$: calcd %C:37.50, %H:1.56, %N:10.93, %S:50.00, found %C:37.68, %H:1.74, %N:10.61, %S:50.42.

EXAMPLE 8

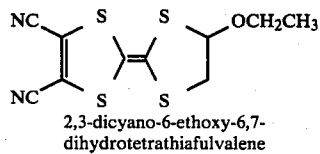

2,3-dicyano-6-ethoxy-6,7-dihydrotetrathiafulvalene

The same reaction conditions as provided in Example 1 are followed, except one mole equivalent of 1,2-dichloroethylethyl ether is used in place of methyl iodide. Work up of the reaction mixture gave 2,3-dicyano-6-ethoxy-6,7-dihydrotetrathiafulvalene as a purple solid; mp 129° C.; mass spectrum, parent ion: 300.

EXAMPLE 9

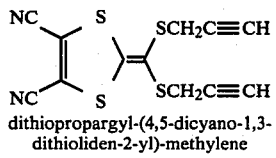

dithiopropargyl-(4,5-dicyano-1,3-dithioliden-2-yl)-methylene

The same reaction conditions as provided in Example 1 are followed, except two mole equivalents of propargyl bromide are used in place of methyl iodide. Work up of the reaction mixture gave dithiopropargyl-(4,5-dicyano-1,3-dithioliden-2-yl)-methylene as an orange-red solid; mp 165°; mass spectrum, parent ion: 306.

EXAMPLE 10

To one equivalent of tetracyanotetrathiafulvalene dissolved in nitrogen-purged acetonitrile is added two mole equivalents of potassium phenylsulfide under nitrogen with stirring. Concentration of the reaction mixture precipitates the dark-brown, air-sensitive salt of dipotassium dithiolate-(4,5-dicyano-1,3-dithioliden-2-yl)-methylene. Further reaction of this salt to dithiomethyl-(4,5-dicyano-1,3-dithioliden-2-yl)-methylene was accomplished by redissolving in acetonitrile and adding excess methyl iodide.

EXAMPLE 11

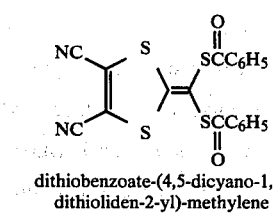

dithiobenzoate-(4,5-dicyano-1,3-dithioliden-2-yl)-methylene

The same reaction conditions as provided in Example 1 are followed, except two mole equivalents of benzol chloride are used in placed of methyl iodide, and florosil is used in place of silica gel in the chromatography on the reaction mixture. Work-up of the reaction mixture gave dithiobenzoate-(4,5-dicyano-1,3-dithioliden-2-yl)-methylene as a dark red solid; mp: 109° C., mass spectrum 438.

EXAMPLE 12

The same reaction conditions as provided in Example 1, except 0.5 mole equivalents of nickel acetate is used in placed of methyl iodide. The triethyl ammonium salt of bis(dithiolate-(4,5-dicyano-1,3-dithioliden-2-yl)-methylene) nickel precipitates from the reaction solution as a black solid; mp: >360° C. The spectrum in dimethylformamide displayed broad visible absorptions at 11,500 and 16,500 A.

EXAMPLE 13

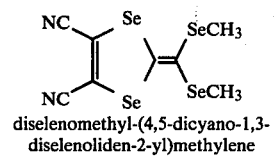

diselenomethyl-(4,5-dicyano-1,3-diselenoliden-2-yl)methylene

The same reaction conditions as provided in Example 1 are followed, except tetracyanotetraselenafulvalene is used in place of tetracyanotetrathiafulvalene. Work-up of the reaction mixture gave diselenomethyl-(4,5-dicyano-1,3-diselenoliden-2-yl)methylene as an orange-red solid; mp 135° C.; mass spectrum parent ion (based on $^{80}Se$): 450.

EXAMPLE 14

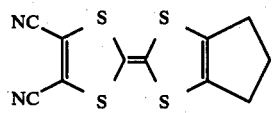

-continued 2,3-dicyano-6,7-trimethylenetetrathiafulvalene

To one mole equivalent of tetracyanotetrathiafulvalene, dissolved in nitrogen-purged acetonitrile, is added two equivalents of sodium thioacetate. After 10 minutes stirring, one mole equivalent of 2-chlorocyclopentanone is added and the reaction mixture stirred for 30 minutes. Evaporation of the solvent gave a dark colored oil which was slowly added to ice-cooled concentrated sulfuric acid. Dilution of the acid solution with large volumes of ether, provided a purple solid which was purified by chromatography (silica gel, hexane-chloroform) to give 2,3-dicyano-6,7-trimethylenetetrathiafulvalene: mp 210° C.; mass spectrum, parent ion 294.

EXAMPLE 15

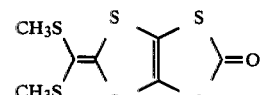

dithiomethyl-(4,5-(2'-oxo-1',3'-dithioleno)-1,3-dithioliden-2-yl)methylene

To one mole equivalent of 2,3-dicyano-6,7-(2'-oxo-1',3'-dithioleno)-(4',5'-h)-tetrathiafulvalene (see structure IV), dissolved in nitrogen-purged acetonitrile in an ice-bath is added dropwise two mole equivalents of triethylamine and phenyl thiol in aceonitrile. After 30 minutes stirring, excess methyl iodide is added and the solvent evaporated. The oily reaction mixture is chromatographed (silica gel, hexane-chloroform) to give dithiomethyl-(4,5-(2'-oxo-1',3'-dithioleno)-1,3-dithioliden-2-yl)methylene as a light olive solid; mp 138° C.; mass spectrum, parent ion 298.

Having thus described our invention, what we claim as new, and desire to secure by Letters Patent is:

1. A new composition of matter diselenomethyl-(4,5-dicyano-1,3-diselenoliden-2-yl)-methylene.

* * * * *